United States Patent
Meyer, III

(10) Patent No.: US 9,907,592 B2
(45) Date of Patent: Mar. 6, 2018

(54) SELF GUIDING SURGICAL BONE FIXATION SCREW

(75) Inventor: Thomas L. Meyer, III, New Albany, OH (US)

(73) Assignee: Syberspine Limited, New Albany, OH (US)

(*) Notice: Subject to any disclaimer, the term of this patent is extended or adjusted under 35 U.S.C. 154(b) by 632 days.

(21) Appl. No.: 13/102,293

(22) Filed: May 6, 2011

(65) Prior Publication Data

US 2012/0283790 A1 Nov. 8, 2012

(51) Int. Cl.
*A61B 17/86* (2006.01)

(52) U.S. Cl.
CPC ........ *A61B 17/8635* (2013.01); *A61B 17/863* (2013.01); *A61B 17/8625* (2013.01)

(58) Field of Classification Search
USPC ........... 606/301–321, 64, 254–265; 411/386, 411/411, 424, 426, 499
See application file for complete search history.

(56) References Cited

U.S. PATENT DOCUMENTS

| 5,234,301 | A  | * | 8/1993  | Grossberndt et al. ........ 411/386 |
| 5,674,224 | A  | * | 10/1997 | Howell et al. .................. 606/88 |
| 6,652,529 | B2 | * | 11/2003 | Swanson ......................... 606/62 |
| 7,232,283 | B2 | * | 6/2007  | Dill et al. ..................... 411/453 |
| 7,780,706 | B2 |   | 8/2010  | Marino et al. |
| 2006/0241600 | A1 |   | 10/2006 | Ensign et al. |
| 2009/0062797 | A1 | * | 3/2009  | Huebner et al. ................ 606/62 |
| 2009/0198291 | A1 |   | 8/2009  | Kevin et al. |

* cited by examiner

*Primary Examiner* — Kevin T Truong
*Assistant Examiner* — Tracy Kamikawa
(74) *Attorney, Agent, or Firm* — Frank H. Foster; Kremblas & Foster

(57) ABSTRACT

A surgical bone fixation screw having a head, an end segment distally from the head and an intermediate shank having outwardly protruding screw threads. The improvement is a self guiding, threadless, elongated end segment having a smooth outer surface with no cutting edges, a length of at least 8 mm and preferably 15 mm and a bluntly rounded end with an outer contour that is smoothly blended to the shank. Most preferably, the bluntly rounded end is substantially a prolate hemispheroid.

6 Claims, 4 Drawing Sheets

FIG. 6
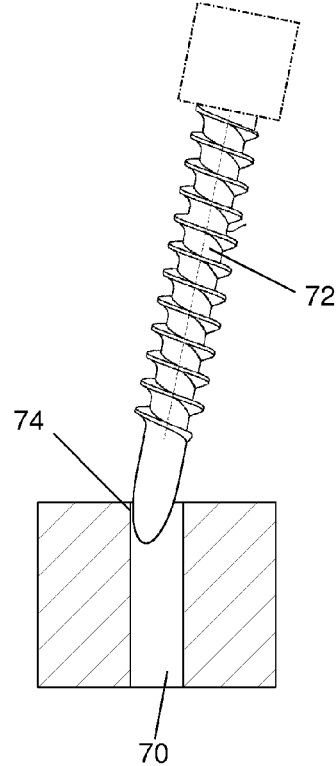
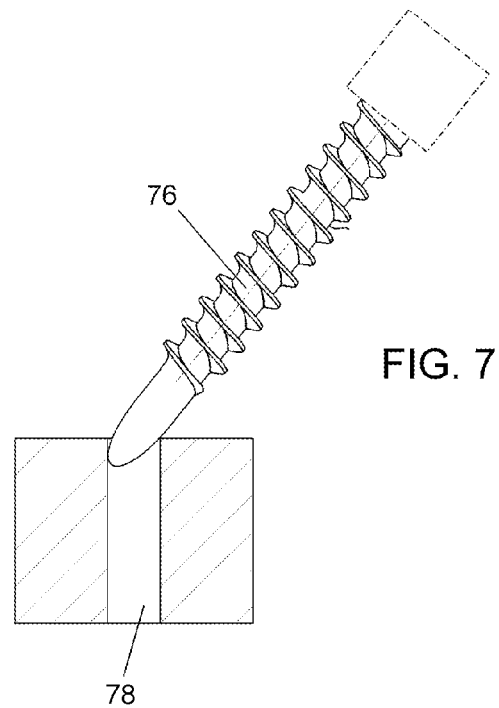
FIG. 7
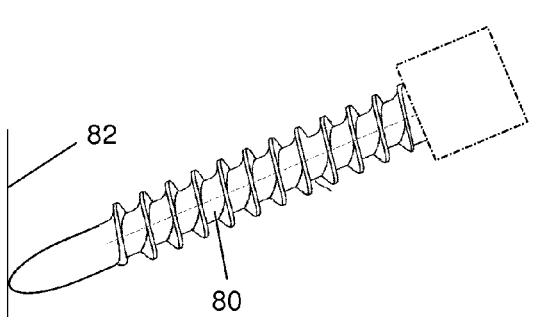
FIG. 8
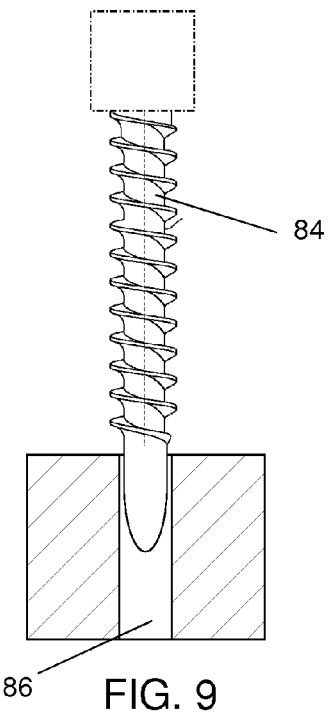
FIG. 9

SELF GUIDING SURGICAL BONE FIXATION SCREW

BACKGROUND OF THE INVENTION

This invention relates generally to medical bone fixation/stabilization systems which are devices that commonly comprise a system of screws, plates and rods that are attached to bones in various surgical procedures. The invention more particularly relates to an improved screw for use in such bone fixation/stabilization systems. The improved screw has structural features that guide the screw along the trajectory of a bore or passageway that has been preformed by a surgeon. The self guiding feature allows the surgery to be performed with a smaller incision that is characteristic of surgical procedures that use a guide wire while allowing the guide wire to be removed prior to insertion of the screw so that complications that sometimes occur when a screw is guided by a guide wire can be avoided.

A common use of bone fixation/stabilization systems is for spinal fixation and stabilization. For this purpose, a spinal fixation system is attached to two or more adjacent vertebrae using pedicle screws to mechanically the attach rods and/or plates to the vertebral bone.

In one prior art spinal fixation procedure, after making an initial incision, the surgeon uses a drill to form a bore in the vertebral bone, then uses a tap to make a female threaded bore and then inserts the screw into the bore. A slight variation eliminates the tap and instead uses a self tapping screw. A disadvantage of this procedure is that a relatively larger incision is made and the soft tissues are distracted to provide access to and a view of the vertebrae.

Another prior art procedure can be performed through a considerably smaller incision. After the initial incision, a guide wire, referred to as a k-wire, is inserted with the assistance of fluoroscopy to position the wire through vertebral bone along a trajectory selected by the surgeon as the desired eventual trajectory of the screw. Fluoroscopy is needed because the small size of the incision impairs the view of the surgeon. The properly positioned k-wire is then used as a guide for guiding a drill, tap and pedicle screw. The drill, tap and the pedicle screw are all cannulated so that they can follow the trajectory of the wire that extends through their central, longitudinal passageway. In this procedure, after the k-wire is positioned, the exposed k-wire is threaded through a drill and/or tap which is then used to form a bore in the vertebral bone. Then the drill and/or tap is removed but the k-wire remains in place. A cannulated pedicle screw, guided by the k-wire along the selected trajectory followed by the wire, is then inserted through the soft tissue and into the bore formed in the vertebral bone. After installation of the pedicle screw, the wire is pulled out. Consequently, once the surgeon has properly positioned the k-wire, the k-wire guides the drill and/or tap and also the pedicle screw along the trajectory of the k-wire, despite the poor visibility available to the surgeon because of the relatively small size of the incision.

One problem that sometime occurs with this k-wire procedure is that before the pedicle screw is installed, the k-wire may be unintentionally dislocated or partially withdrawn. In that event, the surgeon must relocate it. Another problem that sometimes occurs is that, as the pedicle screw is moving along the k-wire during installation, a bend or kink may develop along the k-wire ahead of the direction of insertion of the pedicle screw. Such a bend or kink can catch on the advancing inner end of, and stop further insertion of, the pedicle screw. An even greater problem occurs if the pedicle screw is advanced after it catches on a bend or kink in the k-wire and thereby forces the k-wire through the anterior cortex of the vertebral body and into the aorta and vena cava causing serious medical complications. Consequently, if the pedicle screw becomes jammed against a kink or bend in the k-wire, the screw and the k-wire must be removed and replaced before placement of the screw.

Therefore, it is an object and feature of the invention to provide a surgical bone fixation screw that can be used in a procedure that has the advantage of requiring only the smaller incision that is possible with the k-wire procedure, but is self guiding so that the k-wire can be removed before insertion of the pedicle screw thereby avoiding the above described problems and complications. A bone fixation screw according to the invention provides the new result that the screw is guided by an elongated guide end segment on the distal end of the screw itself, making guidance by a k-wire unnecessary.

BRIEF SUMMARY OF THE INVENTION

The invention is a surgical bone fixation screw that is improved by a self-guiding end segment that is threadless, elongated and has a smooth outer surface with no cutting edges. The end segment has a length of at least 8 mm and preferably 15 mm and has a bluntly rounded end and an outer contour that is smoothly blended to the threaded shank of the screw. Most preferably, the bluntly rounded end is substantially a prolate hemispheroid.

BRIEF DESCRIPTION OF THE SEVERAL VIEWS OF THE DRAWINGS

FIG. 6-9 are views showing an embodiment of the invention in side elevation and illustrating the contacting relationship of the surface configuration and length of the guiding end segment of the invention with surfaces and bores engaged by a screw embodying the invention during an installation procedure.

Figures 1, 2:
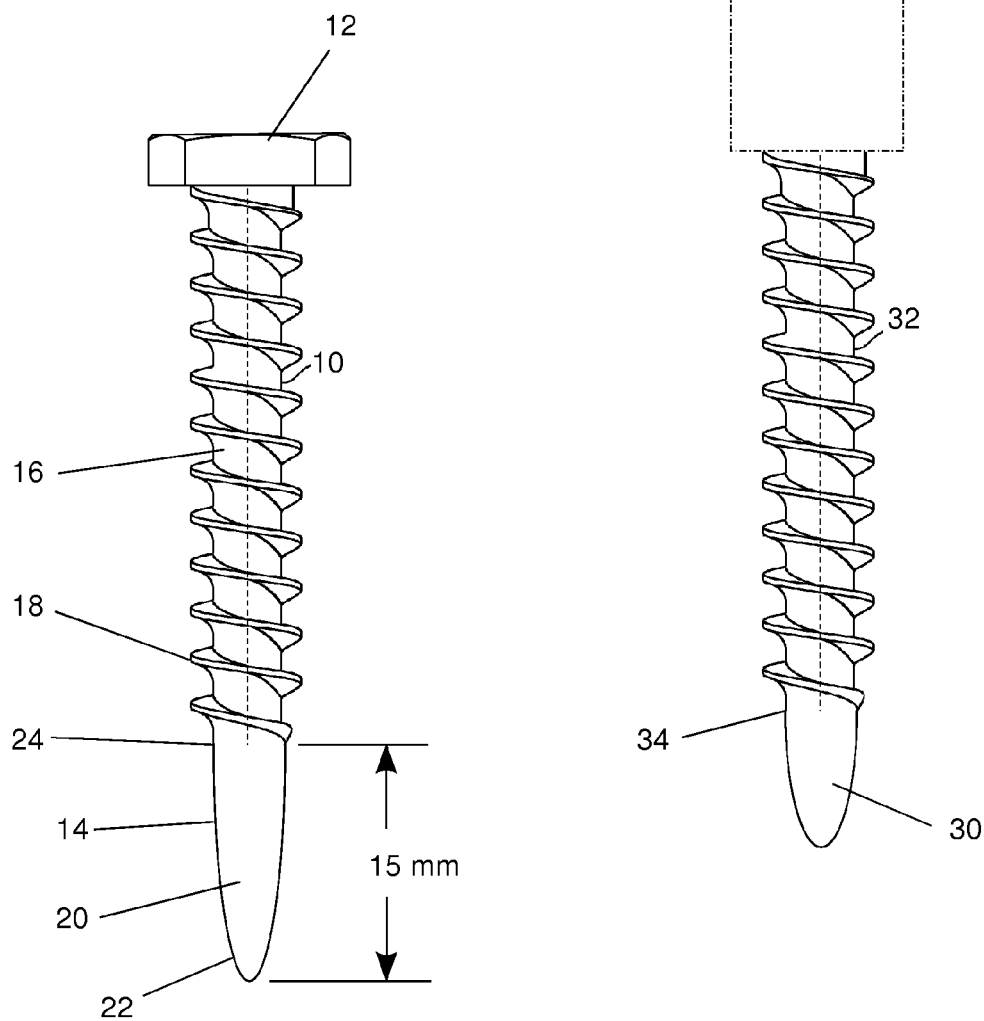
FIG. 1 is a view in side elevation of an embodiment of the invention.
FIG. 2 is a view in side elevation of an alternative embodiment of the invention.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose.

DETAILED DESCRIPTION OF THE INVENTION

Various geometrical terms for three dimensional shapes or surface contours are used in this specification. Although they are known to those skilled in the art and are defined in the prior art in a variety of publications, their definitions are conveniently available on the internet at the web sites of Wikipedia and Wiktionary and easily found by an internet search for the particular terms. Therefore, the definitions are not repeated in this specification.

FIG. 1 illustrates an improved surgical bone fixation screw 10 that embodies the invention. The screw 10 has a head 12 at its proximal end. There are a substantial variety of screw heads for bone fixation screws that are used in the prior art and which may be used on embodiments of the invention. A simple hex head 12 is illustrated in FIG. 1 but other heads may be substituted because this invention is not directed to any aspect of the screw head. Consequently, the heads of the other screws illustrated in the drawings are illustrated as a simple box in phantom. The invention is directed to the structure of the unthreaded distal end of the bone fixation screw which distinguishes the invention from the prior art.

An end segment 14 is located at the distally opposite end from the head 12. An intermediate shank 16, having outwardly protruding screw threads 18, is interposed between and connects the head 12 and the end segment 14. The structure of the end segment 14 makes the screw 10 self-guiding during a surgical installation procedure. The improved end segment 14 is a threadless, elongated, guiding end segment 14 having a smooth outer surface 20 with no cutting edges. The guiding end segment 14 has a length of at least 8 mm, a bluntly rounded end 22 and an outer contour that is smoothly blended to the cylindrical shank 16 at their junction 24. Although experimental installations of screws embodying the invention indicated that the length of the guiding end segment 14 should be at least 8 mm, those experiments also indicated that the optimally effective guiding end segment 14 is about or substantially 15 mm as illustrated in FIG. 1. However, it is also believed that a guiding end segment length in the range of 12 to 17 mm is also quite effective.

Although 15 mm is believed to be the optimum length of the guiding end segment, that length is not critical because some other lengths will provide the benefits of the invention, even if they are somewhat less effective. The farther from the optimum length, the less effective is the self guidance. That is why a range of effective lengths is described. The desired length is necessarily made by the subjective judgment of the surgeon who performs the procedures using the screws. It appears from the experiments that a length shorter than 8 mm is insufficiently effective. Although a length longer than 15 mm or 17 mm is effective, any greater length does not seem to increase the effectiveness of the self guidance and instead merely adds unnecessary, excess length that does not improve the self guidance and can reduce the length of the screw threads on the shank.

It is very important that the guiding end segment of the invention be threadless. The absence of threads along the entire guiding end segment prevents the leading end of the screw from digging into the wall of the bore and resisting an initial, manual, longitudinal push of the screw into the preformed bore by the surgeon. Because of the length of the guiding end segment, the screw threads on the shank engage the bore in the bone only after the surgeon has positioned the screw in substantial alignment with the bore. This feature is important because such positioning must be done by feel, without the advantage of seeing the entrance of the screw into the bore. The term "threadless" means that there are no screw threads on the guiding end segment. Threads are relatively sharp, helically arranged ridges that protrude outwardly from a surface so that they can engage a surrounding material and function to retain the screw in the material. The addition of one or more small grooves, valleys or protrusions on the guiding end segment that do not function as threads would not make the guiding end segment threaded.

The bluntly rounded end is a surface contour that is substantially a three-dimensional quadratic surface. Preferably it is a hemiellipsoid and most preferably it is substantially a prolate hemispheroid. Although a prolate hemispheroid is preferred, small, insubstantial variations from a perfect prolate hemispheroid can be made without significant deterioration of the effectiveness of the invention which would still operates according to principles of the invention. Consequently, the word "substantially" is used to encompass minor, insubstantial variations that do not make the self guiding characteristic of the guiding end segment ineffective.

The bluntly rounded end could be an elliptic paraboloid that is smoothly blended to the shank at its open end or, if a frusto-cylindrical or frusto-conical shank extension (subsequently described) is used, smoothly blended to that shank extension. However, the paraboloid is not preferred because of the need for a substantial blend.

It is desirable that adjoining surface contours be "smoothly blended" at their intersection. When two three dimensional objects having differing geometric shapes are joined, for example an object with a conical surface joined to an object with a cylindrical surface, they may have a line or edge of intersection at which tangents to their respective surfaces make a discontinuous transition at the junction of the two objects. In other words, there is a relatively sharp rim or edge that is identifiable at the junction of the two surfaces. However, that rim or edge can be rounded off to provide a more gradual transition from one surface to the other. Such a rounded off transition provides a smoothly blended contour transition from one surface to the other. Consider, for example, a hemisphere or a prolate hemispheroid joined to a cylinder with the diameter of the hemisphere or the minor axis of the prolate hemispheroid being identical. In that example, there is a smooth transition at the junction of the two and no rounding off is needed to make the junction of the two smoothly blended. However, if a cylinder is joined to a surface that is less than half of a sphere or half of a prolate spheroid, even if the open end of each has a lateral dimension equal to the diameter of the cylinder, there will be a rim at their junction. The same is true for a conical surface joined to a cylindrical surface. It is desirable that the surface contour transition at the junction be rounded off to provide a smoothly blended contour at the junction. Of course, some minor discontinuity in the surface contour transition at the junction can be tolerated if it is sufficiently minor and insubstantial.

Another characteristic of a guiding end segment on screws embodying the invention is that is has a smooth outer surface with no cutting edges. This means that the guiding end segment has no longitudinal cutting edges such as present on self tapping screws and also has longitudinally adjacent surfaces that are sufficiently blended that there are no circumferential sharp edges. A self tapping screw is an example of a screw with longitudinal cutting edges. Such edges are to be avoided on the guiding end segment of the invention because they can cut into the soft tissue and preformed bore through bone and cause the screw to pierce or cut into the wall of the bore or path through the soft tissue and deviate from the preformed trajectory into the soft tissue or bone.

FIG. 2 illustrates an embodiment of the invention that has a guiding end segment 30 that differs from the embodiment of FIG. 1 because it is shorter. However, like the embodiment of FIG. 1, the entire guiding end segment 30 is a prolate hemispheroid and is joined to the shank 32 at a junction 34. The minor axis of the prolate hemispheroidal guiding end segment 30 is equal to the minor or interior diameter of the cylindrical shank 32. Consequently, there is no rim or edge at their junction 34.

Figure 3:
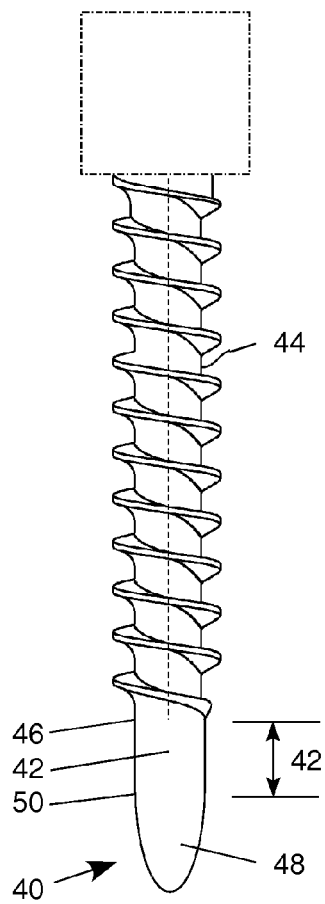
FIG. 3 is a view in side elevation of another alternative embodiment of the invention.

FIG. 3 illustrates an alternative configuration for the guiding end segment of the invention. In FIG. 3, the guiding end segment 40 has a frusto-cylindrical (cylinder with a finite length) shank extension segment 42 that is joined to the shank 44 at a junction 46. A prolate hemispheroidal portion 48 is joined to the opposite end of the frusto-cylindrical portion 42 at a junction 50. Because the diameter of the shank 44, the diameter of the shank extension segment 42 and the length of the minor axis of the prolate hemispheroidal portion 48 are all identical, they blend together without the need for rounding off.

Figure 4:
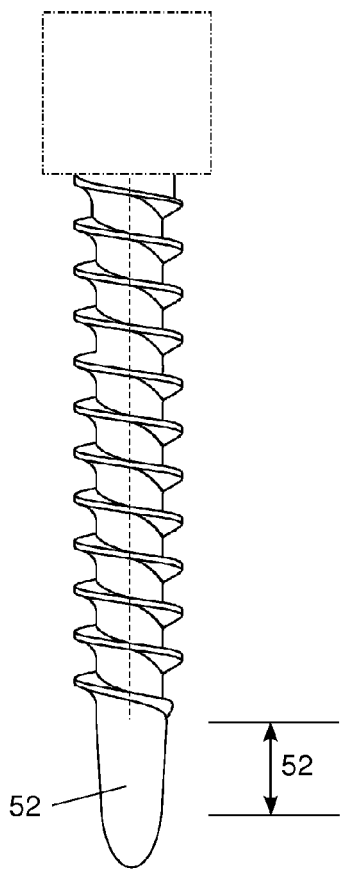
FIG. 4 is a view in side elevation of yet another alternative embodiment of the invention.

FIG. 4 illustrates another alternative configuration for the guiding end segment of the invention. In FIG. 4, a frusto-conical shank extension segment 52 has been substituted for the frusto-cylindrical shank extension segment 42 of FIG. 3. The result is that there is a small taper in the shank extension segment 52.

Figure 5:
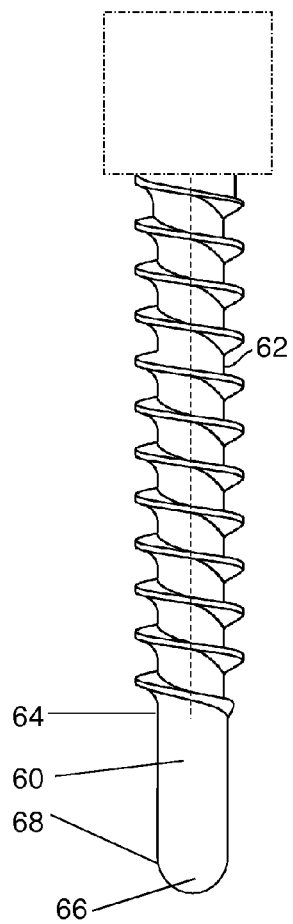
FIG. 5 is a view in side elevation of still another alternative embodiment of the invention.

FIG. 5 illustrates yet another alternative configuration for the guiding end segment of the invention. A frusto-cylindrical shank extension segment 60 is smoothly blended to the shank 62 at a junction 64. A hemispherical end 66 is smoothly blended to the shank extension 60 at a junction 68. Although it is believed that a hemispherical end is serviceable, it is not preferred.

The use of a bone fixation pedicle screw having a guiding end segment of the invention for a spinal fixation begins in the conventional manner. The patient is positioned prone on the patient's belly with his or her back up. Fluoroscopy is positioned to provide an anterior-posterior view or lateral view. A small incision is made and a guide wire (k-wire) is inserted and positioned against a pedicle with its position being verified with fluoroscopy. In one of the several ways known in the prior art, a k-wire is driven into vertebral bone to the final depth desired for the pedicle screw. The surgeon then forms a bore into the bone to create a passageway along a track that follows a desired trajectory. The bore is formed by using a cannulated drill and tap guided by the k-wire. Alternatively, the bore can be formed without use of the wire guide by using a pedicle probe (sometimes referred to as a "gearshift"). With both procedures, a passageway is formed through soft tissue, through a pedicle and into the vertebral body. If the guide wire procedure is used, as is preferred, the guide wire is removed at this stage, unlike the prior art k-wire procedure.

The surgeon then begins to insert the distal guiding end segment of the bone fixation screw into the preformed passage though the soft tissue and into the preformed bore in the bone. This is initially done with a longitudinal thrust without rotation of the screw until the threads of the screw engage the bore in the bone. As the surgeon advances the screw, the soft tissues, skin and muscle etc. push radially on the screw with a force that urges misalignment of the screw. The guiding end segment deflects the soft tissue wall of the passage rather than piercing and traveling into the soft tissue and also allows the tissue to apply a force to the screw to deflect its trajectory and maintain its alignment in the passage and along the desired trajectory. More importantly, when the guiding end segment begins to engage the bone, because it has no point or sharp edges and the screw threads are offset from the tip end of the guiding end segment by at least 8 mm and preferably 15 mm, the screw is deflected away from the wall of the bore and toward alignment in the central longitudinal axis of the bore. That is particularly important when the guiding end segment contact the softer cancellous inner part of the bone.

The curvature of the guiding end segment, particularly the prolate hemispheroidal surface, causes a surface of the guiding end segment that engages a wall of the bore, to be at an angle with the bore wall that maximizes the centering force applied by the bore wall against the screw. The portion of the surface of the screw that extends from the point of contact with the bore wall toward the direction of screw advance desirably is at an acute angle with the wall in order to get a ramping action that deflects the end of the screw toward the central axis of the bore. The length of the unthreaded guiding end segment assures that all sharp edges and points are far enough behind the distal tip end of the screw as the screw advances along the preformed passage so that, whenever the screw end advances obliquely against a wall of the bore, the end segment, and therefore the axis of the screw, is deflected by the wall of the bore rather than digging into or piercing the wall of the bore. The length and contour characteristics of the guiding end segment of the screw urges the screw toward the center of the preformed bore so that it advances along the intended trajectory without having been deflected or misdirected through the bore wall and out of the trajectory of the bore.

FIGS. 6-9 illustrate the above advantages of the length and contour of the guiding end segment of the invention. In FIG. 6, the screw 72 is positioned at a more acute angle with the interior wall of the bore 70 because it is more nearly coaxially aligned in the bore 70. The interior wall of the bore 70 contacts the screw 72 at a contact point 74. The surface of the screw 72 which is more advanced into the bore 70 than the contact point 74 curves progressively and smoothly further away from the wall of the bore 70 as that surface extends further into the bore 70. That prevents the end of the screw from penetrating the wall of the bore and instead ramps the end of the screw away from the wall of the bore as the screw is advanced into the bore 70.

In FIG. 7, although the axis of the screw 76 is at a greater angle to the axis of the bore 78, that same relationship of the surface of the screw at the contact point with the wall of the bore 78 still exists.

FIG. 8 illustrates that, even at the very large angle between the axis of the screw 80 and the wall 82 of the bore, that same relationship of the surface of the screw at the contact point with the wall of the bore still exists. The existence of that same relationship despite the differing angles between the wall of the bore and the longitudinal axis of the screw is what makes the guiding end segment of the invention so effective in guiding the screw trajectory, despite the absence of a k-wire.

FIG. 9 illustrates that, because of the length and smooth, threadless contour of the guiding end segment of the invention, the screw 84 can be firmly aligned in the bore 86 in a manner that is clearly discernable by feel with the hands of the surgeon.

Figure 10:
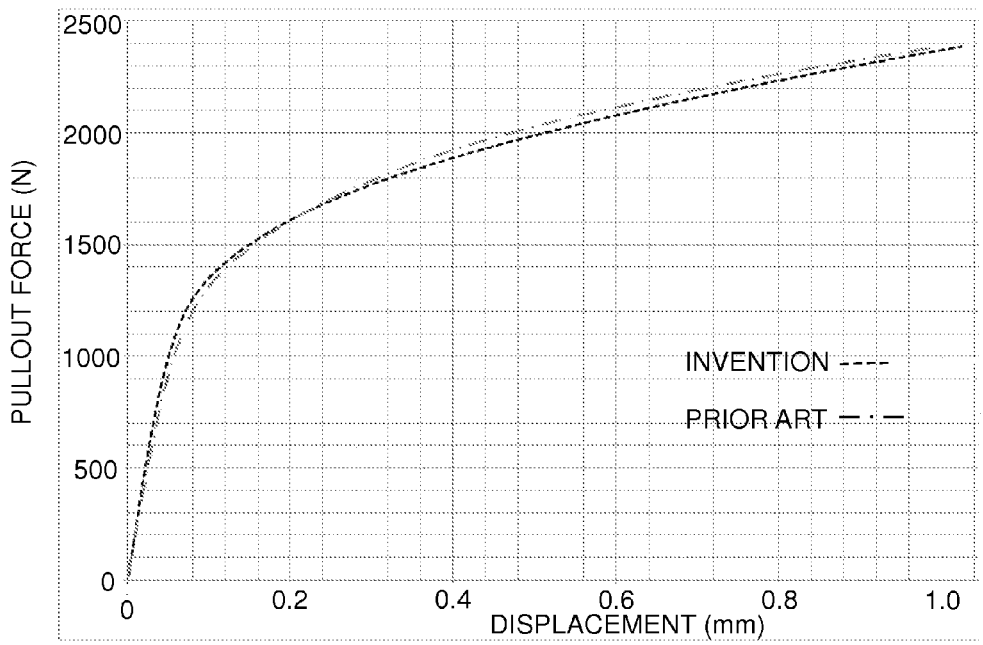
FIG. 10 is a graph of the pullout force vs. displacement that is comparing a prior art screw to a screw embodying the invention.
Figure 11:
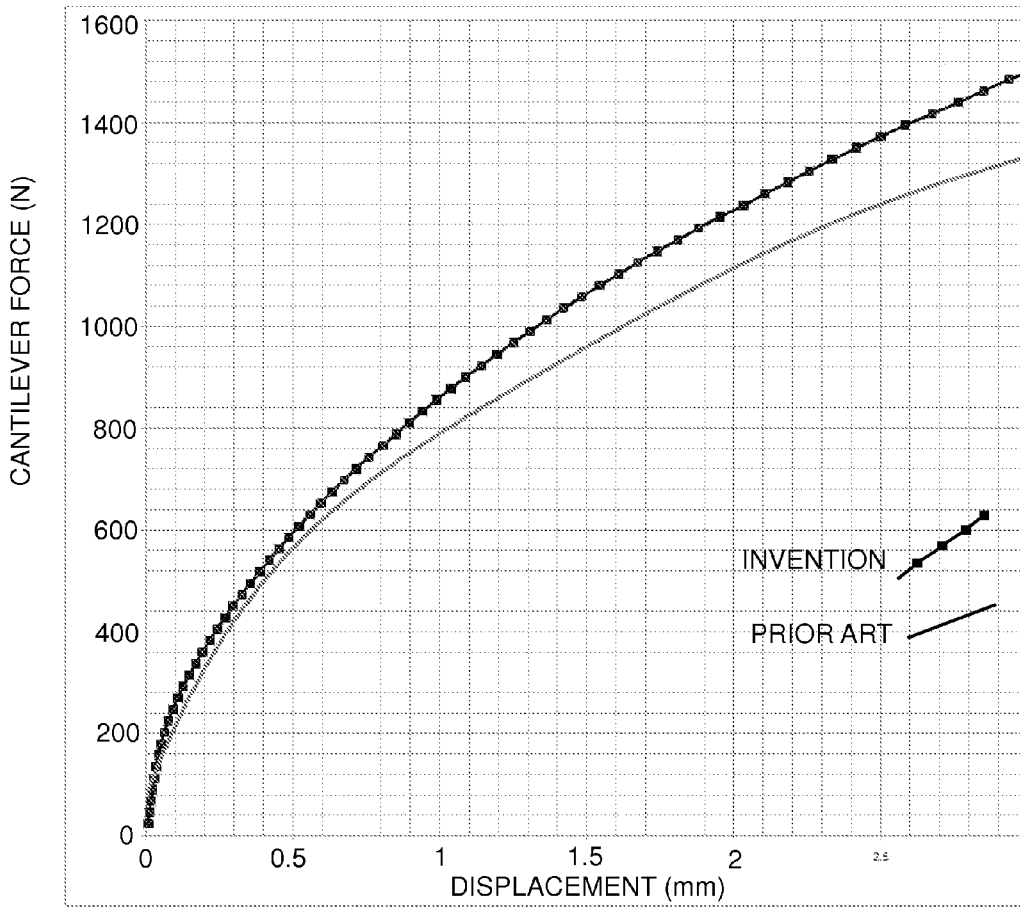
FIG. 11 is a graph of the cantilever force vs. displacement that is comparing a prior art screw to a screw embodying the invention.

Tests data was obtained by finite element analysis to determine the resistance of embodiments of the invention to movement after being installed in comparison to the resistance of a prior art screws to such movement. The test data is shown in FIGS. 10 and 11. The concern was whether a fixation screw embodying the invention might have less resistance to movement because it has a considerably larger portion of its length without screw threads or other means for grasping the surrounding bone. A person skilled in the art would be expected to regard the screw threads as the principal structures that operate to retain the screw within the bone. Two type of tests were performed. One test measured screw displacement as a function of pullout force. A pullout force is a force applied along the longitudinal axis of the screw. The other test measured screw displacement as a function of a cantilever force. A cantilever force is a force applied along a radial from the longitudinal axis of the screw.

FIG. 10 shows pullout force vs. displacement. As can be observed from FIG. 10, the screw embodying the invention performed essentially identically to the prior art screw. This is believed to be because the relative hardness of the outer cortical bone applies nearly all the force on the screw that resists pullout of the screw. The guiding end segment of the invention is located in the softer cancellous bone after the screw is in its final position. Because of its softness, the cancellous bone can not offer much resistance to pullout of the screw.

FIG. 11 shows cantilever force vs. displacement. As can be observed from FIG. 11, the surprising result was that the screw embodying the invention performed a little better than the prior art screw. An explanation may be that, because the guiding end segment is large and has a smooth rounded outer surface with no cutting edges, the radial force applied by the bone to the guiding end segment is more uniformly distributed across that outer surface. That is particularly important in the softer cancellous bone in which the guiding end segment is located after the screw is in its final position.

Therefore, the conclusion can be drawn that not only is a fixation screw embodying the invention more easily installed with reduced risk of problems and complications, but also its retention strength in the bone is a least as good as a prior art screw and, with respect to cantilever forces, appears to have a somewhat increased retention strength.

This detailed description in connection with the drawings is intended principally as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The invention claimed is:

1. An improved surgical bone fixation screw having a bone fixation screw head, an end segment distally from the head and an intermediate shank having outwardly protruding screw threads, the intermediate shank being interposed between and connecting the head and the end segment, wherein the improvement makes the screw self-guiding during a surgical installation procedure and comprises:
   the threads of the intermediate shank extending continuously along the intermediate shank to the end segment; and
   the end segment formed adjacent the screw threads of the intermediate shank as a threadless, elongated, guiding end segment having a smooth outer surface with no cutting edges, the end segment also having
   (a) a length of at least 8 mm; and
   (b) a bluntly rounded end that is smoothly and directly blended to the intermediate shank and having no identifiable junction with the intermediate shank, wherein the bluntly rounded end is a shape selected from the group consisting of a three-dimensional quadratic surface, a hemiellipsoid, a prolate hemispheroid, and an elliptic paraboloid.

2. The self guiding bone fixation screw in accordance with claim 1 wherein the length of the end segment is in the range of 12 to 17 mm.

3. The self guiding bone fixation screw in accordance with claim 2 wherein the length of the end segment is 15 mm.

4. An improved surgical bone fixation screw having a bone fixation screw head, an end segment distally from the head and an intermediate shank having outwardly protruding screw threads, the intermediate shank being interposed between and connecting the head and the end segment, wherein the improvement makes the screw self-guiding during a surgical installation procedure and comprises:
   the threads of the intermediate shank extending continuously along the intermediate shank to the end segment; and
   the end segment formed adjacent the screw threads of the intermediate shank as a threadless, elongated, guiding end segment having a smooth outer surface with no cutting edges, the end segment also having
   (a) a length of at least 8 mm;
   (b) a single frusto-cylindrical or frusto-conical shank extension segment having an outer contour that is smoothly and directly blended to the intermediate shank and has no identifiable junction with the intermediate shank; and
   (c) a bluntly rounded end smoothly and directly blended to the shank extension segment and having no identifiable junction with the shank extension segment wherein the bluntly rounded end is a prolate hemispheroid.

5. The self guiding bone fixation screw in accordance with claim 4 wherein the length of the end segment is in the range of 12 to 17 mm.

6. The self guiding bone fixation screw in accordance with claim 5 wherein the length of the end segment is 15 mm.

* * * * *